(12) United States Patent
Lanter et al.

(10) Patent No.: US 7,595,409 B2
(45) Date of Patent: Sep. 29, 2009

(54) 3,4-DIAMINO-3-CYCLOBUTENE-1,2-DIONE DERIVATIVES AS POTASSIUM CHANNEL OPENERS

(75) Inventors: James C. Lanter, Norristown, PA (US); Zhihua Sui, Norristown, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 22 days.

(21) Appl. No.: 11/693,167

(22) Filed: Mar. 29, 2007

(65) Prior Publication Data

US 2007/0232689 A1 Oct. 4, 2007

Related U.S. Application Data

(60) Provisional application No. 60/788,382, filed on Mar. 31, 2006.

(51) Int. Cl.
*C07D 307/94* (2006.01)

(52) U.S. Cl. .................................................... 549/345

(58) Field of Classification Search .................. 549/345
See application file for complete search history.

(56) References Cited

OTHER PUBLICATIONS

Butera J.A. et al.: "Design and SAR of Novel Potassium Channel Openers Targeted for Urge Urinary Incontinence.1. N-Cyanoguanidine Biososteres Processing in Vivo Bladder Selectivity". Journal of Medicinal Chemistry, American Chemical Society, Washington, US, vol. 43, No. 6, Feb. 2000, pp. 1187-1202, XP002168956.

Gilbert A.M. et al.: "Design and SAR of Novel Potassium Channel Openers Targeted for Urge Urinary Incontinence.2. Selective and Potent Benzylamino Cyclobutendiones". Journal of Medicinal Chemistry, American Chemical Society, Washington, US, vol. 43, No. 6, Feb. 2000, pp. 1203-1214, XP002444717.

*Primary Examiner*—Janet L. Andres
*Assistant Examiner*—Raymond Covington
(74) *Attorney, Agent, or Firm*—Jeremy K Mckown

(57) ABSTRACT

The present invention is directed to novel 3,4-diamino-3-cyclobutene-1,2-dione derivatives, pharmaceutical compositions containing them and their use in the treatment of disorders related to potassium channel.

7 Claims, No Drawings

3,4-DIAMINO-3-CYCLOBUTENE-1,2-DIONE DERIVATIVES AS POTASSIUM CHANNEL OPENERS

RELATED APPLICATIONS

This application claims the benefit under 35 USC §119(e) of provisional application Ser. No. 60/788,382, filed Mar. 31, 2006, which is incorporated herein in its entirety.

FIELD OF THE INVENTION

The present invention is directed to novel 3,4-diamino-3-cyclobutene-1,2-dione derivatives, pharmaceutical compositions containing them and their use in the treatment of potassium channel related disorders. The compounds of the invention are thus useful for treatment of various disorders. This includes but is not limited to urinary incontinence, overactive bladder, hypertension, erectile dysfunction, female sexual disorders, dysmenorrhea, irritable bowl syndrome, airway hyperactivity, epilepsy, stroke, Alzheimer's and Parkinson's diseases, myocardial injury, coronary artery disease as well as hair loss and baldness.

BACKGROUND OF THE INVENTION

Ion channels play a fundamental role in the hormeostasis of cell function through the regulation of the transmembrane movement of ions. Cellular activity can be affected by modifications of the activities of the ion channels. This leads to changes in membrane potential difference. Potassium channels are a diverse and ubiquitous group of ion channels. They principally regulate the resting membrane potential of the cell and attenuate the level of excitation of cells. A functional $K_{ATP}$ channel is a hetero-octamer assembled from four inward rectifying potassium channel subunits (Kir6.2) and four sulfonylurea receptor (SUR) subunits. There are two SUR genes, SUR1 and SUR2. SUR1/Kir6.2 channels are found in the pancreas and brain. Two major splice variants arise from the SUR2 gene, SUR2A and SUR2B, that differ only at the C-terminal 42 amino acids. SUR2A/Kir6.2 channels are found in cardiac and skeletal tissues whereas SUR2B/Kir6.2 channels are found in smooth muscles of many tissues including bladder (Aguilar-Bryan, 1998). A number of diseases or conditions may be treated with potassium channel openers. This includes overactive bladder, urinary incontinence, male erectile dysfunction, female sexual disorders, premature labor, benign prostate hyperplasia (BPH), dysmenorrhea, neurodegeneration, stroke, pain, coronary artery disease, angina, ischemia, eating disorders, irritable bowl syndrome, alopecia.

Urinary incontinence (UI) is a disease that can affect the overall quality of life of a patient. Overactive bladder (OAB) is the most prevalent form of UI, with reported prevalence rate from 40 to 70% of all diagnosed UI cases (Wein, 2000). OAB is characterized by the symptoms of increased urinary frequency, urgency, and involuntary loss of urine. A primary cause of OAB is an oversensitive bladder that contracts unexpectedly and involuntarily. The ideal pharmaceutical agent should suppress the involuntary contraction while leaving the normal voiding contractions intact. ATP-sensitive potassium channel openers (KCO) could serve as such agents. The ATP-sensitive potassium channels ($K_{ATP}$) are expressed in bladder smooth muscle and function as key regulators of the resting membrane potential in these cells. Compounds that selectively open these channels hyperpolarize the cell and decrease cellular excitability, resulting in suppression of involuntary bladder contractions, while leaving the normal micturition circuitry intact.

SUMMARY OF THE INVENTION

The present invention is directed to compounds of formula (I)

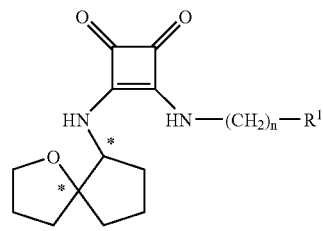

wherein n is an integer from 0 to 2;

$R^1$ is selected from the group consisting of cycloalkyl, aryl and heteroaryl; wherein the aryl or heteroaryl is optionally substituted with one or more substituents independently selected from the group consisting of halogen, hydroxy, amino, $C_{1-4}$alkylamino, di($C_{1-4}$alkyl)amino, cyano, nitro, $C_{1-4}$alkyl, $C_{1-4}$alkoxy, halogen substituted $C_{1-4}$alkyl and halogen substituted $C_{1-4}$alkoxy;

and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating disorders related to ion channels, preferably a potassium ion channel, more preferably an ATP-sensitive potassium ion channel, comprising administering, to a subject in need thereof, a therapeutically effective amount of any of the compounds or pharmaceutical compositions described above.

An example of the invention is a method for treating a disorder selected from the group consisting of urinary incontinence, overactive bladder, hypertension, erectile dysfunction, female sexual disorders, dysmenorrhea, irritable bowl syndrome, airway hyperactivity, epilepsy, stroke, Alzheimer's disease, Parkinson's disease, myocardial injury, coronary artery disease, hair loss and baldness, preferably urinary incontinence, comprising administering, to a subject in need thereof, an effective amount of any of the compounds or pharmaceutical compositions described above.

Another example of the invention is the use of any of the compounds described herein in the preparation of a medicament for treating: (a) urinary incontinence, (b) overactive bladder, (c) hypertension, (d) erectile dysfunction, (e) female sexual disorders, (f) dysmenorrhea, (g) irritable bowl syndrome, (h) airway hyperactivity, (i) epilepsy, (j) stroke, (k) Alzheimer's disease, (l) Parkinson's disease, (m) myocardial injury, (n) coronary artery disease, (o) hair loss or (p) baldness, in a subject in need thereof.

DETAILED DESCRIPTION OF THE INVENTION

The present invention is directed to compounds of formula (I)

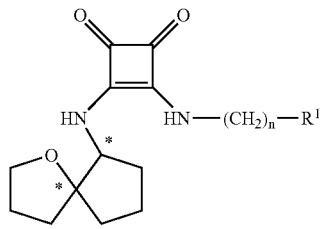

wherein n and $R^1$ are as herein defined. The compounds of the present invention are ion channel openers, more specifically potassium channels openers. The compounds of the present are thus useful for the treatment of various disorders including, but not limited to, urinary incontinence, overactive bladder, hypertension, erectile dysfunction, female sexual disorders, dysmenorrhea, irritable bowl syndrome, airway hyperactivity, epilepsy, stroke, Alzheimer's and Parkinson's diseases, myocardial injury, coronary artery disease as well as hair loss and baldness. Preferably, the compounds of the present invention are useful in the treatment of urinary incontinence or overactive bladder.

In an embodiment of the present invention, n is an integer from 0 to 1. In another embodiment of the present invention, n is an integer from 1 to 2.

In an embodiment of the present invention, $R^1$ is selected from the group consisting of cycloalkyl, aryl and 5- to 6 membered heteroaryl; wherein the aryl or heteroaryl is optionally substituted with one or more substituents independently selected from the group consisting of halogen, amino, $C_{1-4}$alkylamino, di($C_{1-4}$alkyl)amino, cyano, nitro, $C_{1-4}$alkyl and fluorine substituted $C_{1-4}$alkyl.

In another embodiment of the present invention, $R^1$ is selected from the group consisting of cycloalkyl, phenyl and 6-membered heteroaryl; wherein the aryl or heteroaryl is optionally substituted with one to three substituents independently selected from the group consisting of halogen, $C_{1-4}$alkyl, fluorine substituted $C_{1-4}$alkyl and cyano.

In another embodiment of the present invention, $R^1$ is selected from the group consisting of cyclohexyl, 1-adamantyl, phenyl, 4-chlorophenyl, 3,4-dichloro-phenyl, 2-fluorophenyl, 2-trifluoromethyl-phenyl, 3-trifluoromethyl-phenyl, 3,5-bis(trifluoromethyl)-phenyl, 2-ethyl-4-cyano-phenyl, 2,4-dichloro-6-methyl-phenyl and 5-cyano-pyrid-2-yl.

In another embodiment of the present invention, $R^1$ is selected from the group consisting of phenyl, 4-chlorophenyl, 3-trifluoromethyl-phenyl, 2-ethyl-4-cyano-phenyl and 2,4-dichloro-6-methyl-phenyl.

In another embodiment of the present invention, n is 0 and $R^1$ is 2-ethyl-4-cyano-phenyl.

Additional embodiments of the present invention, include those wherein the substituents selected for one or more of the variables defined herein (i.e. n and $R^1$) are independently selected to be any individual substituent or any subset of substituents selected from the complete list as defined herein.

Representative compounds of the present invention are as listed in Table 1 below. In an embodiment of the present invention is any single compound or subset of compounds selected from the representative compounds listed in Tables 1 below.

TABLE 1

Representative Compounds of Formula (I)

| ID# | R | n | MS (MH+) |
|---|---|---|---|
| 1 | 2-ethyl-4-cyano-phenyl | 0 | 366 |
| 2 | 5-cyano-pyrid-2-yl | 0 | 339 |
| 3 | 2,4-dichloro-6-methyl-phenyl | 1 | 410 |
| 4 | 4-chloro-phenyl | 1 | 362 |
| 5 | phenyl | 1 | 327 |
| 6 | 3-trifluoromethyl-phenyl | 1 | 395 |
| 7 | phenyl | 2 | 341 |
| 8 | cyclohexyl | 1 | 332 |
| 9 | 3,4-dichloro-phenyl | 1 | 396 |
| 10 | 1-adamantyl | 1 | 385 |
| 11 | 2-fluoro-phenyl | 1 | 345 |
| 12 | 2-trifluoromethyl-phenyl | 1 | 395 |
| 13 | 3,5-bis(trifluoromethyl)-phenyl | 1 | 463 |

As used herein, "halogen" shall mean chlorine, bromine, fluorine and iodine. Preferably, the halogen is chlorine, bromine or fluorine, more preferably, chlorine or fluorine.

As used herein, the term "alkyl" whether used alone or as part of a substituent group, include straight and branched chains. For example, alkyl radicals include methyl, ethyl, n-propyl, isopropyl, n-butyl, isobutyl, sec-butyl, t-butyl, pentyl and the like. Similarly, the term "$C_{1-4}$alkyl" whether used alone or as part of a substituent group, include straight and branched chains containing 4 carbon atoms. For example, methyl, ethyl, n-propyl, isopropyl, n-butyl, isobutyl, sec-butyl and t-butyl.

As used herein, unless otherwise noted, "alkoxy" whether used alone or as part of a substituent group, shall denote an oxygen ether radical of the above described straight or branched chain alkyl groups. For example, methoxy, ethoxy, n-propoxy, sec-butoxy, t-butoxy, n-hexyloxy and the like. Similarly, the term "$C_{1-4}$alkoxy" whether used alone or as part of a substituent group, shall denote an oxygen ether radical of the above described straight or branched chain $C_{1-4}$alkyl groups. For example, methoxy, ethoxy, n-propoxy, sec-butoxy, t-butoxy, and the like.

As used herein, unless otherwise noted, the term "halogen substituted $C_{1-4}$alkyl" shall mean any $C_{1-4}$alkyl group as defined above substituted with at least one halogen atom, preferably substituted with a least one fluoro atom. Suitable examples include but are not limited to —$CF_3$, —$CHF_2$, —$CH_2$—$CF_3$, —$CF_2$—$CF_2$—$CF_2$—$CF_3$, and the like.

As used herein, unless otherwise noted, the term "fluorine substituted $C_{1-4}$alkyl" shall mean any $C_{1-4}$alkyl group as defined above substituted with at least one fluorine atom, preferably one to three fluorine atoms. Suitable examples include but are not limited to —$CF_3$, —$CHF_2$, —$CH_2$—$CF_3$, —$CF_2$—$CF_2$—$CF_2$—$CF_3$, and the like.

As used herein, unless otherwise noted, the term "halogen substituted $C_{1-4}$alkoxy" shall mean any $C_{1-4}$alkoxy group as defined above substituted with at least one halogen atom, preferably substituted with a least one fluoro atom. Suitable examples include but are not limited to —$OCF_3$, —$OCHF_2$, —$OCH_2$—$CF_3$, —$OCF_2$—$CF_2$—$CF_2$—$CF_3$, and the like.

As used herein, unless otherwise noted, the term "fluorine substituted $C_{1-4}$alkoxy" shall mean any $C_{1-4}$alkoxy group as defined above substituted with at least one fluorine atom, preferably one to three fluorine atoms. Suitable examples include but are not limited to —$OCF_3$, —$OCHF_2$, —$OCH_2$—$CF_3$, —$OCF_2$—$CF_2$—$CF_2$—$CF_3$, and the like.

As used herein, unless otherwise noted, the term "cycloalkyl" shall mean any stable monocyclic, bicyclic, polycyclic or bridged saturated ring system, for example cyclopropyl, cyclobutyl, cyclopentyl, cyclohexyl, cycloheptyl and cyclooctyl, tetrahydronaphthyl, adamantyl, and the like.

As used herein, unless otherwise noted, "aryl" shall refer to unsubstituted carbocyclic aromatic groups such as phenyl, naphthyl, and the like. Preferably, the aryl group is phenyl or naphthyl, more preferably, phenyl.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. Preferably, the heteroaryl contains 5- to 6-ring atoms (i.e. the heteroaryl groups is a 5- to 6-membered heteroaryl), more preferably, the heteroaryl contains 6-ring atoms (i.e. the heteroaryl group is a 6-membered heteroaryl). The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, pyrazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like. Preferably, the heteroaryl group is pyridyl.

As used herein, the notation "*" shall denote the presence of a stereogenic center.

When a particular group is "substituted" (e.g., aryl, heterocycloalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

Under standard nomenclature used throughout this disclosure, the terminal portion of the designated side chain is described first, followed by the adjacent functionality toward the point of attachment. Thus, for example, a "phenyl-$C_{1-4}$ alkyl-amino-carbonyl-$C_{1-4}$alkyl-" substituent refers to a group of the formula

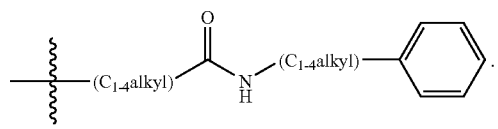

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Compounds of formula (I) of the present invention may be prepared according to the process outlined in Scheme 1 as follows:

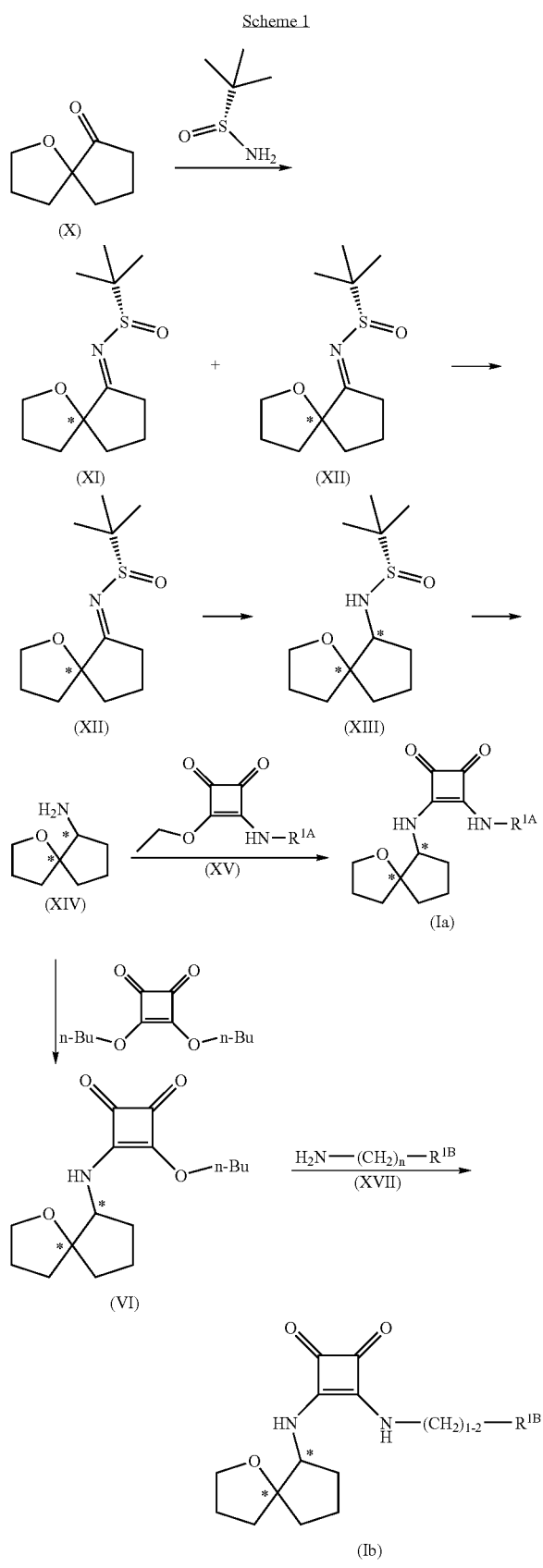

Scheme 1

Accordingly, a suitably substituted compound of formula (X), a known compound or a compound prepared by known methods, is reacted with R-tert-butylsulfinamide (also known as 2-methyl-propane-2-sulfinic acid amide), in the presence of titanium (IV) ethoxide, titanium (IV) isopropoxide, and the like, a known compound (which acts as both a catalyst and dehydrating agent), a known compound, in an organic solvent such as THF, tetrahydropyran, and the like preferably in THF, to yield a mixture of the corresponding compounds of formulas (XI) and (XII).

The mixture of compounds of formula (XI) and (XII) are preferably separated according to known methods, for example by chromatography, to yield the less polar compound of formula (XI) and the more polar compound of formula (XII).

The more polar compound of formula (XII) is reacted with a suitably selected reducing agent such as sodium borohydride, and the like, in a mixture of organic solvents such as tetrahydrofuran (THF) and an alcohol such as methanol, ethanol, and the like, to yield the corresponding compound of formula (XIII) as a single diastereomer.

The compound of formula (XIII) is reacted with an acid such as HCl in dioxane or an acid such as trifluoroacetic acid (TFA) in dichloromethane (DCM), and the like, to yield the compound of formula (XIV).

The compound of formula (XIV) is reacted with a suitably compound of formula (XV), wherein $R^{1A}$ is optionally substituted aryl or optionally substituted heteroaryl (as herein defined), a known compound or compound prepared by known methods, in an organic solvent such as ethanol, isopropanol, and the like, at a temperature greater than about room temperature, preferably at about reflux temperature, to yield the corresponding compound of formula (Ia).

Alternatively, the compound of formula (IV) is reacted with di-n-butyl-squarate (wherein the abbreviation "n-Bu" in the structure represents n-butyl), a known compound, in an organic solvent such as THF, tetrahydropyran, and the like, at room temperature, to yield the corresponding compound of formula (XVI).

The compound of formula (XVI) is reacted with a suitably substituted compound of formula (XVII), wherein when n is 1 or 2 then $R^{1B}$ is cycloalkyl, optionally substituted aryl or optionally substituted heteroaryl (as herein defined) and when n is 0 then $R^{1B}$ is cycloalkyl (as herein defined), a known compound or compound prepared by known methods, in an organic solvent such as THF, tetrahydropyran, and the like, at room temperature, to yield the corresponding compound of formula (Ib).

Where the processes for the preparation of the compounds according to the invention give rise to mixture of stereoisomers, these isomers may be separated by conventional techniques such as preparative chromatography.

The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

One skilled in the art will recognize that wherein a reaction step of the present invention may be carried out in a variety of solvents or solvent systems, said reaction step may also be carried out in a mixture of the suitable solvents or solvent systems.

The present invention includes within its scope "prodrugs" of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The present invention includes within its scope "pharmaceutically acceptable salts" of the compounds of this invention. For use in medicine, the salts of the compounds of this invention refer to non-toxic pharmaceutically acceptable salts. Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 50-100 mg and may be given at a dosage of from about 0.1-5.0 mg/kg/day, preferably from about 0.5-2.5 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating of the present invention may also be carried out using a pharmaceutical composition comprising any of the compounds as defined herein and a pharmaceutically acceptable carrier. The pharmaceutical composition may contain between about 0.1 mg and 500 mg, preferably about 50 to 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders as described herein is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day. Preferably, the range is from about 0.5 to about 5.0 mg/kg of body weight per day, most preferably, from about 1.0 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

2-methyl-N-[1-oxaspiro[4.4]non-6-ylidene]-2-propanesulfinamide

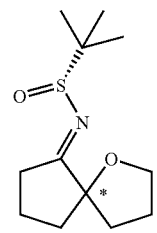

1-Oxa-spiro[4.4]nonan-6-one (2.53 g, 18.0 mmol) and R-tert-butylsulfinamide (2.20 g, 18.1 mmol) were dissolved in anhydrous THF (40 mL). Titanium ethoxide (8.17 g, ~20% in ethanol) was introduced and the reaction mixture heated to 74° C. overnight. After cooling, the reaction mixture was poured onto cold brine (50 mL) and extracted with ethyl acetate. The organic layers were combined and concentrated in vacuo to yield a yellow residue. The residue was purified by flash chromatography into the less polar and more polar isomers. The title compound, the more polar isomer was isolated as a colorless oil and used in the next reaction step without further purification. (Note: The less polar isomer was also isolated, as a residue). (Note: the exact stereo-configuration of the N—S bond in the title compound was not determined.)

More Polar Isomer:
$^1$H NMR (300 MHz, CDCl$_3$) δ 3.96 (t, J=7.0 Hz, 2H); 3.05-2.94 (m, 1H); 2.73-2.62 (m, 1H); 2.21-1.72 (series of m, 8H); 1.26 (s, 9H)

Less Polar Isomer:
$^1$H NMR (300 MHz, CDCl$_3$) δ4.00-3.87 (m, 2H); 3.16-3.05 (m, 1H); 2.64-2.58 (m, 1H); 2.21-1.66 (series of m, 8H); 1.26 (s, 9H)

EXAMPLE 2

2-methyl-N-(1-oxaspiro[4.4]non-6-yl)-2-propanesulfinamide

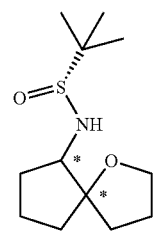

A solution of the compound prepared in Example 1 above (1.73 g, 7.10 mmol) in THF (50 mL) was treated with a solution of sodium borohydride (462 mg, 12.2 mmol) in methanol (10 mL). After stirring for 45 min at room temperature, the reaction was quenched by the addition of saturated ammonium chloride (10 mL) and the resulting mixture was extracted with ethyl acetate. The reaction mixture was then concentration, and the residue was purified by flash chromatography to yield the title compound as a colorless oil.

MS (m/Z)=245 (MH+) $^1$H NMR (300 MHz, CDCl$_3$) δ 3.92 (br d, J=5.0 Hz, 1H); 3.89-3.77 (m, 2H); 3.40 (q, J=6.1 Hz, 1H); 2.11-1.41 (series of m, 10H); 1.21 (s, 9H)

EXAMPLE 3

1-oxaspiro[4.4]nonan-6-amine

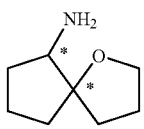

A solution of the compound prepared as in Example 2 above (1.53 g, 6.23 mmol) in dioxane (20 mL) was treated with 4N HCl in dioxane (16 mL). After heating to 45° C. for 30 minutes, the reaction mixture was concentrated in vacuo, the residue triturated with diethyl ether and the solid collected by filtration to yield the title compound as its corresponding hydrochloride salt, as a white solid. The title compound was isolated as a single diastereomer, although the absolute stereo-configuration was not determined.

MS (m/Z)=142 (MH+) $^1$H NMR (300 MHz, DMSO-d6) δ 7.81 (br s, 3H), 3.85-3.62 (m, 2H); 3.26 (t, J=7.4 Hz, 1H); 2.04-1.49 (series of m, 10H)

EXAMPLE 4

3-ethyl-4-[[2-(1-oxaspiro[4.4]non-6-ylamino)-3,4-dioxo-1-cyclobutene-1-yl]amino]-benzonitrile (Compound 1)

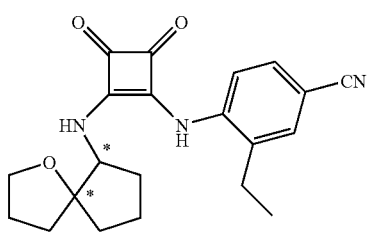

A solution of 4-(2-ethoxy-3,4-dioxo-cyclobut-1-enzylamino)-3-ethyl-benzonitrile (60 mg, 0.22 mmol) in ethanol was treated with a solution of the hydrochloride salt prepared as in Example 3 above (40 mg, 0.22 mmol) in ethanol (5 mL). The reaction mixture was treated with 1 equivalent of sodium methoxide in methanol to free-base the amine and then heated to reflux for 3 hours. After cooling, water was added to the reaction mixture and the resulting precipitated was collected by filtration to yield the title compound as a solid.

MS (m/Z)=366 (MH+)

EXAMPLE 5

3-butoxy-4-(1-oxaspiro[4.4]non-6-ylamino)-3-cyclobutene-1,2-dione

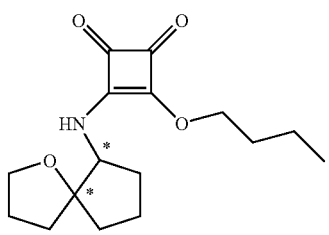

A solution of di-n-butylsquarate (0.15 mL, 0.69 mmol) and the hydrochloride salt compound prepared as in Example 3 above (116 mg, 0.65 mmol) in dry THF was treated with 1 equivalent of sodium methoxide. After stirring the reaction mixture at room temperature for 20 hours, the title compound was collected by filtration as a precipitate and used in the next reaction step without further purification.

EXAMPLE 6

3-[[(2,4-dichloro-6-methylphenyl)methyl]amino]-4-(1-oxaspiro[4.4]non-6-ylamino)-3-cyclobutene-1,2-dione (Compound 3)

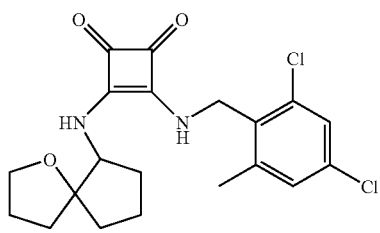

A solution of the compound prepared as in Example 5 above (0.12 g, 0.41 mmol) in dry THF (5 mL) was treated with 2,4-dichloro-6-methyl benzyl amine (0.11 g, 0.56 mmol) and the resulting mixture stirred at room temperature for 20 hours. The title compound was collected by filtration as a solid.

MS (m/Z)=410 (MH+)

Additional compounds of the present invention were similarly prepared according to the procedures described in Scheme 1 and the Examples above.

EXAMPLE 7

Potassium Channel Assay

TE671 human medulloblastoma cells were obtained from ATCC and grown in Dulbecco's modified Eagle's medium (DMEM) supplemented with 10% fetal bovine serum, 100 U/ml penicillin and 100 U/ml streptomycine.

The day before testing, the cells were plated in black 96-well plates at 50 K/well. On the day of testing, the growth media was removed, then 100 μl of FLIPR buffer (20 mM 4-(2-hydroxyethyl)-1-piperizine ethane sulfonic acid (HEPES), 120 mM NaCl, 2 mM KCl, 2 mM CaCl$_2$, 1 mM MgCl$_2$, 5 mM Glucose) and 100 μl of Membrane Potential Assay Dye (Molecular Devices) dissolved in FLIPR buffer were added to each well. The cells were incubated at room temperature for 15 to 30 min.

The effect of test compounds on KATP channels were evaluated on a fluorometric imaging plate reader (FLIPR, Molecular Devices) at room temperature. After a baseline period, 50 µl of 5× stock solution of test compound prepared in FLIPR buffer was added and fluorescent change was monitored for 3 minutes. After this reading, glyburide, a KATP channel blocker, was added to a final concentration of 5 µM to check the specificity of the test compound as a KATP channel openers. Hyperpolarization resulting from KATP channel opening was observed as a decrease in fluorescent intensity.

Representative compounds of the present invention were tested according to the procedure described above, with results as listed in Table 2 below.

TABLE 2

| ID No | % Stimulation @ 30 µM |
|---|---|
| 1 | 94 |
| 2 | 25 |
| 3 | 49 |
| 4 | 40 |
| 5 | 26 |
| 6 | 25 |
| 7 | 19 |
| 8 | 5 |
| 9 | 20 |
| 10 | 23 |
| 11 | 19 |
| 12 | 12 |
| 13 | 22 |

EXAMPLE 8

As a specific embodiment of an oral composition, 100 mg of Compound No. 1, prepared as in Example 4 above, is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

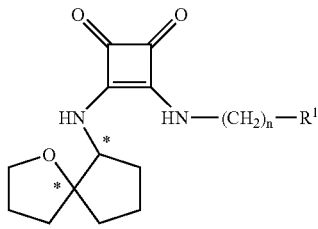

wherein n is an integer from 0 to 2;

$R^1$ is selected from the group consisting of cycloalkyl, aryl and heteroaryl wherein said hereroarly contains one heteroatom;

wherein the aryl or heteroaryl is optionally substituted with one or more substituents independently selected from the group consisting of halogen, hydroxy, amino, $C_{1-4}$alkylamino, di($C_{1-4}$alkyl)amino, cyano, nitro, $C_{1-4}$alkyl, $C_{1-4}$alkoxy, halogen substituted $C_{1-4}$alkyl and halogen substituted $C_{1-4}$alkoxy;

or a pharmaceutically acceptable salt thereof.

2. A compound as in claim 1, wherein n is an integer from 0 to 2;

$R^1$ is selected from the group consisting of cycloalkyl, aryl and 5- to 6 membered heteroaryl;

wherein the aryl or heteroaryl is optionally substituted with one or more substituents independently selected from the group consisting of halogen, amino, $C_{1-4}$alkylamino, di($C_{1-4}$alkyl)amino, cyano, nitro, $C_{1-4}$alkyl and fluorine substituted $C_{1-4}$alkyl;

or a pharmaceutically acceptable salt thereof.

3. A compound as in claim 2, wherein n is an integer from 0 to 2;

$R^1$ is selected from the group consisting of cycloalkyl, phenyl and 6-membered heteroaryl;

wherein the aryl or heteroaryl is optionally substituted with one to three substituents independently selected from the group consisting of halogen, $C_{1-4}$alkyl, fluorine substituted $C_{1-4}$alkyl and cyano;

or a pharmaceutically acceptable salt thereof.

4. A compound as in claim 3, wherein n is an integer from 0 to 2;

$R^1$ is selected from the group consisting of cyclohexyl, 1-adamantyl, phenyl, 4-chlorophenyl, 3,4-dichlorophenyl, 2-fluorophenyl, 2-trifluoromethyl-phenyl, 3-trifluoromethyl-phenyl, 3,5-bis(trifluoromethyl)-phenyl, 2-ethyl-4-cyano-phenyl, 2,4-dichloro-6-methyl-phenyl and 5-cyano-pyrid-2-yl;

or a pharmaceutically acceptable salt thereof.

5. A compound as in claim 4, wherein n is an integer from 0 to 1;

$R^1$ is selected from the group consisting of phenyl, 4-chlorophenyl, 3-trifluoromethyl-phenyl, 2-ethyl-4-cyanophenyl and 2,4-dichloro-6-methyl-phenyl;

or a pharmaceutically acceptable salt thereof.

6. A compound as in claim 4, selected from the group consisting of 3-ethyl-4-[[2-(1-oxaspiro[4.4]non-6-ylamino)-3,4-dioxo-1-cyclobutene-1-yl]amino]-benzonitrile and pharmaceutically acceptable salts thereof.

7. A pharmaceutical composition comprising a pharmaceutically acceptable carrier and a compound of claim 1.

* * * * *